US011565726B2

(12) United States Patent
Yang et al.

(10) Patent No.: US 11,565,726 B2
(45) Date of Patent: Jan. 31, 2023

(54) VEHICLE AND SAFE DRIVING ASSISTANCE METHOD THEREFOR

(71) Applicants: Hyundai Motor Company, Seoul (KR); Kia Motors Corporation, Seoul (KR)

(72) Inventors: Dong Il Yang, Seoul (KR); Eun Young Choi, Seoul (KR); Ki Seok Seong, Chungcheongnam-do (KR); Min Sang Yu, Gyeonggi-do (KR); Hyeong Jin Ham, Gyeonggi-do (KR); Rosali Sun Pyun, Gyeonggi-do (KR); Jin Su Jeong, Gyeonggi-do (KR); Woo Jin Kim, Incheon (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 240 days.

(21) Appl. No.: 17/020,315

(22) Filed: Sep. 14, 2020

(65) Prior Publication Data

US 2021/0362750 A1    Nov. 25, 2021

(30) Foreign Application Priority Data

May 21, 2020   (KR) .................. 10-2020-0060848

(51) Int. Cl.
*B60W 60/00*    (2020.01)
*A61B 5/18*    (2006.01)
(Continued)

(52) U.S. Cl.
CPC ............ *B60W 60/0059* (2020.02); *A61B 5/18* (2013.01); *A61B 5/6893* (2013.01); *B60R 25/10* (2013.01); *B60R 25/24* (2013.01); *B60R 25/25* (2013.01); *B60W 40/08* (2013.01); *B60W 60/0051* (2020.02); *G06V 20/597* (2022.01);
(Continued)

(58) Field of Classification Search
CPC ............ B60W 60/0059; B60W 40/08; B60W 60/0051; B60W 2040/0836; B60W 2040/0845; B60W 2540/22; B60W 2540/24; B60W 2540/26; B60W 40/09; B60W 50/14; B60W 2050/143; B60W 60/0016; B60W 2040/0872; B60W 2040/089; A61B 5/18; A61B 5/6893; A61B 5/4845; A61B 5/024; A61B 5/1116; A61B 5/0022; A61B 5/112; A61B 5/1128; A61B 5/163; A61B 5/4803; A61B 2503/22; A61B 5/7275; A61B 5/746; B60R 25/10; B60R 25/24; B60R 25/25; B60R 25/241;
(Continued)

(56) References Cited

U.S. PATENT DOCUMENTS 9,135,803 B1 * 9/2015 Fields .................... G08B 21/02
9,440,657 B1 * 9/2016 Fields .................. B60K 28/066
(Continued)

*Primary Examiner* — Peter D Nolan
*Assistant Examiner* — Peter Y Ning
(74) *Attorney, Agent, or Firm* — Fox Rothschild LLP

(57) ABSTRACT

A vehicle includes a processing device that detects an authentication device approaching the vehicle, determines a user's impaired state based on user condition information acquired using at least one device mounted on the vehicle, and performs a safe driving assistance service. The safe driving assistance service can prevent an impaired user from operating the vehicle.

18 Claims, 8 Drawing Sheets

| CLASSIFICATION | ELEMENT | WEIGHT | REFERENCE VALUE (START FROM 0 POINT) | DETAILED SCORING CRITERIA (0 ~10 POINTS, USE OF SLIDING SCALE) | NOTE |
|---|---|---|---|---|---|
| SMARTPHONE | SMARTPHONE DETERMINATION INFORMATION | 0.2 | 0 | SMARTPHONE DRINKING/DRUG DETERMINATION SYSTEM SCORE | |
| FRONT/REAR CAMERA | STAGGERING | 0.05 | NO STAGGERING | +1 POINT FOR EVERY 1°/S ON AVERAGE (10°/S: 10 POINTS) | |
| | WALKING SPEED | 0.025 | 4kph | +1 POINT FOR EVERY -0.2kph (BELOW 2kph: 10 POINTS) | |
| SPEECH RECOGNITION | TONE | 0.05 | 5kHz | +1 POINT FOR EVERY 1 kHz (OVER 15 kHz: 10 POINTS) | DOMINANT FREQUENCY REFERENCE |
| | dB | 0.05 | 40dBA | +1 POINT FOR EVERY 3dB (OVER 70 dB: 10 POINTS) | BASED ON DRIVER'S SEAT MEASUREMENT |
| | USE OF SPECIFIC WORD | 0.05 | NO USE OF SPECIFIC WORD | +1 POINT FOR EACH APPEARANCE OF WORDS SUCH AS "DRINK WELL," "ALCOHOL," "ONE GLASS OF DRINK," "TWO GLASSES OF DRINK," "I DRUNK," "CALL DESIGNATED DRIVER," "WHEN DESIGNATED DRIVER COMES," "I CAN DO IT," "IT IS NOT LONG TO DESTINATION" (10 OR MORE TIMES: 10 POINTS) | |
| DRIVER MONITORING SYSTEM | NECK ANGLE (DROWSY CONDITION) | 0.1 | NO DROWSINESS | +10 POINTS FOR OCCURRENCE OF DROWSINESS | |
| | EYE BLINKING | 0.1 | NO DROWSINESS | +10 POINTS FOR OCCURRENCE OF DROWSINESS | |
| | REDNESS DEGREE | 0.025 | PREVIOUSLY MEASURED VALUE | +1 POINT DEPENDING ON DEGREE OF EYE REDNESS | NEED TO REVIEW DETAILED CRITERIA |
| BIOMETRICS | HEART RATE | 0.025 | PREVIOUSLY MEASURED VALUE | +1 POINT FOR EVERY 10% INCREASE (INCREASE OF 100%: 10 POINTS) | NORMAL: 10 to 100 bpm |
| | PULSE RATE | 0.025 | PREVIOUSLY MEASURED VALUE | +1 POINT FOR EVERY 10% INCREASE (INCREASE OF 100%: 10 POINTS) | NORMAL: 60 to 90 bpm |
| BIG DATA | TIME PLACE HISTORY | 0.05 | 0 POINT BASED ON BIG DATA | SCORE CALCULATION BASED ON COMPARISON WITH ALL CITIZEN BIG DATA AFTER COMPARISON OF TIME/PLACE INFORMATION FROM START OFF TO AGAIN START ON (0 TO 10 POINTS) | NEED FOR PREVIOUS ANALYSIS OF BIG DATA INFORMATION FOR WASTED RATE OF DRINKING BY TIME/PLACE |
| VEHICLE HISTORY | EXISTING SCORE | 0.025 | 0 POINT | EXISTING AVERAGE SCORE | |
| | NUMBER OF WARNINGS | 0.025 | ZERO NUMBER OF TIMES | +1 POINT PER ONE WARNING (10 TIMES OR MORE: 10 POINTS) | |
| USER HISTORY | EXISTING SCORE | 0.1 | 0 POINT | EXISTING AVERAGE SCORE | |
| | NUMBER OF WARNINGS | 0.1 | ZERO NUMBER OF TIMES | +1 POINT PER ONE WARNING (10 TIMES OR MORE: 10 POINTS) | |
| TOTAL STORE | | 1 | – | 0 ~ 10 POINT | |

(51) Int. Cl.
*A61B 5/00* (2006.01)
*B60R 25/24* (2013.01)
*B60R 25/25* (2013.01)
*B60R 25/10* (2013.01)
*B60W 40/08* (2012.01)
*G06V 20/59* (2022.01)

(52) U.S. Cl.
CPC .... *A61B 5/4845* (2013.01); *B60W 2040/0836* (2013.01); *B60W 2040/0845* (2013.01); *B60W 2540/22* (2013.01); *B60W 2540/24* (2013.01); *B60W 2540/26* (2013.01)

(58) Field of Classification Search
CPC ...... G06V 20/597; G06V 20/58; G06V 40/15; G06V 40/25
See application file for complete search history.

(56) References Cited

U.S. PATENT DOCUMENTS

| | | | | |
|---|---|---|---|---|
| 9,775,565 | B1* | 10/2017 | Berg-Neuman | B60W 40/08 |
| 9,884,628 | B1* | 2/2018 | Grant | B60W 40/08 |
| 10,596,903 | B2* | 3/2020 | DeVries | B60R 25/002 |
| 10,909,476 | B1* | 2/2021 | Sanchez | G08G 1/202 |
| 11,157,906 | B1* | 10/2021 | Smith | G06Q 20/405 |
| 2007/0296601 | A1* | 12/2007 | Sultan | A61B 5/082 |
| | | | | 340/576 |
| 2009/0268022 | A1* | 10/2009 | Omi | A61B 5/18 |
| | | | | 348/135 |
| 2010/0108425 | A1* | 5/2010 | Crespo | A61B 5/082 |
| | | | | 180/272 |
| 2011/0304465 | A1* | 12/2011 | Boult | B60K 28/06 |
| | | | | 340/576 |
| 2013/0345921 | A1* | 12/2013 | Al-Ali | A61B 5/6893 |
| | | | | 600/323 |
| 2014/0002798 | A1* | 1/2014 | Harris | H04M 1/0266 |
| | | | | 455/566 |
| 2014/0222253 | A1* | 8/2014 | Siegel | B60R 16/037 |
| | | | | 701/2 |
| 2014/0231166 | A1* | 8/2014 | Miller | B60K 28/06 |
| | | | | 180/272 |
| 2014/0276090 | A1* | 9/2014 | Breed | A61B 5/7282 |
| | | | | 600/473 |
| 2015/0066284 | A1* | 3/2015 | Yopp | H04W 76/50 |
| | | | | 701/29.2 |
| 2015/0314681 | A1* | 11/2015 | Riley, Sr. | B60K 28/066 |
| | | | | 340/576 |
| 2016/0001781 | A1* | 1/2016 | Fung | G16H 50/20 |
| | | | | 701/36 |
| 2017/0001598 | A1* | 1/2017 | Pophale | B60R 25/243 |
| 2019/0389485 | A1* | 12/2019 | Collins, II | G06V 40/13 |
| 2020/0372271 | A1* | 11/2020 | Hanson | A61B 5/0077 |
| 2021/0291650 | A1* | 9/2021 | Minjeur | A61B 5/163 |
| 2022/0126864 | A1* | 4/2022 | Moustafa | B60W 60/001 |

* cited by examiner

| CLASSIFICATION | ELEMENT | WEIGHT | REFERENCE VALUE (START FROM 0 POINT) | DETAILED SCORING CRITERIA (0~10 POINTS, USE OF SLIDING SCALE) | NOTE |
|---|---|---|---|---|---|
| SMARTPHONE | SMARTPHONE DETERMINATION INFORMATION | 0.2 | 0 | SMARTPHONE DRINKING/DRUG DETERMINATION SYSTEM SCORE | |
| FRONT/REAR CAMERA | STAGGERING | 0.05 | NO STAGGERING | +1 POINT FOR EVERY 1°/S ON AVERAGE (10°/S: 10 POINTS) | |
| | WALKING SPEED | 0.025 | 4kph | +1 POINT FOR EVERY -0.2kph (BELOW 2kph:10 POINTS) | |
| SPEECH RECOGNITION | TONE | 0.05 | 5kHz | +1 POINT FOR EVERY 1 kHz (OVER 15 kHz : 10 POINTS) | DOMINANT FREQUENCY REFERENCE |
| | dB | 0.05 | 40dBA | +1 POINT FOR EVERY 3dB (OVER 70 dB:10 POINTS) | BASED ON DRIVER'S SEAT MEASUREMENT |
| | USE OF SPECIFIC WORD | 0.05 | NO USE OF SPECIFIC WORD | +1 POINT FOR EACH APPEARANCE OF WORDS SUCH AS "DRINK WELL" "ALCOHOL", "ONE GLASS OF DRINK", "TWO GLASSES OF DRINK", "I DRUNK", "CALL DESIGNATED DRIVER", "WHEN DESIGNATED DRIVER COMES", "I CAN DO IT", "IT IS NOT LONG TO DESTINATION" (10 OR MORE TIMES: 10 POINTS) | |
| DRIVER MONITORING SYSTEM | NECK ANGLE (DROWSY CONDITION) | 0.1 | NO DROWSINESS | +10 POINTS FOR OCCURRENCE OF DROWSINESS | |
| | EYE BLINKING | 0.1 | NO DROWSINESS | +10 POINTS FOR OCCURRENCE OF DROWSINESS | |
| | REDNESS DEGREE | 0.025 | PREVIOUSLY MEASURED VALUE | +1 POINT DEPENDING ON DEGREE OF EYE REDNESS | NEED TO REVIEW DETAILED CRITERIA |
| BIOMETRICS | HEART RATE | 0.025 | PREVIOUSLY MEASURED VALUE | +1 POINT FOR EVERY 10% INCREASE (INCREASE OF 100%: 10 POINTS) | NORMAL: 10 to 100 bpm |
| | PULSE RATE | 0.025 | PREVIOUSLY MEASURED VALUE | +1 POINT FOR EVERY 10% INCREASE (INCREASE OF 100%: 10 POINTS) | NORMAL: 60 to 90 bpm |
| BIG DATA | TIME PLACE HISTORY | 0.05 | 0 POINT BASED ON BIG DATA | SCORE CALCULATION BASED ON COMPARISON WITH ALL CITIZEN BIG DATA AFTER COMPARISON OF TIME/PLACE INFORMATION FROM START OFF TO AGAIN START ON (0 TO 10 POINTS) | NEED FOR PREVIOUS ANALYSIS OF BIG DATA INFORMATION FOR MATED RATE OF DRINKING BY TIME/PLACE |
| VEHICLE HISTORY | EXISTING SCORE | 0.025 | 0 POINT | EXISTING AVERAGE SCORE | |
| | NUMBER OF WARNINGS | 0.025 | ZERO NUMBER OF TIMES | +1 POINT PER ONE WARNING (10 TIMES OR MORE: 10 POINTS) | |
| USER HISTORY | EXISTING SCORE | 0.1 | 0 POINT | EXISTING AVERAGE SCORE | |
| | NUMBER OF WARNINGS | 0.1 | ZERO NUMBER OF TIMES | +1 POINT PER ONE WARNING (10 TIMES OR MORE: 10 POINTS) | |
| TOTAL STORE | | 1 | - | 0 ~ 10 POINT | |

FIG. 4

<PRE-CHECK> SMARTPHONE DETERMINATION: THERE IS DRUNKEN POSSIBILITY PATTERN FOLLOWING SCORE : FAILURE (40%)
<MAIN CHECK> DECREASE IN WALKING SPEED (2kph) + USE OF SPECIFIC WORDS ("I ONLY ATE TWO GLASSES, I WASN'T DRUNK, I CAN DO IT MAN"
       └(2-4)/(-0.2)=10 POINTS                                                                           └USE THREE TIMES: 3 POINTS INCREASE IN dB (70 dBA) + NECK ANGLE (OCCURRENCE OF DROWSINESS) + EYE BLINKING ((OCCURRENCE OF DROWSINESS) + BIG DATA INFORMATION (GANGNAM/FRIDAY PM 19 TO 22)
       └(70-40)*(1/3)=+10 POINTS         └OCCURRENCE OF DROWSINESS:+10 POINTS   └OCCURRENCE OF DROWSINESS:+10 POINTS                            └+9 POINTS
VEHICLE HISTORY (AVERAGE SCORE/NUMBER OF WARNINGS) + USER HISTORY (AVERAGE SCORE/NUMBER OF WARNINGS)
                  └AVERAGE : +1 POINTS  └TOTAL THREE TIMES : +3 POINTS     └AVERAGE : +3 POINTS   └TOTAL THREE TIMES : +5 POINTS
△TOTAL SCORE (APPLICATION OF WEIGHT)=8*0.2+10*0.025+3*0.05+10*0.05+
                                    10*0.1+10*0.1+9*0.05+1*0.025+3*0.025+3*0.1+5*0.1=5.85 POINTS

FIG. 5

VEHICLE AND SAFE DRIVING ASSISTANCE METHOD THEREFOR

CROSS-REFERENCE TO RELATED APPLICATION

This application claims under 35 U.S.C. § 119(a) the benefit of Korean Patent Application No. 10-2020-0060848, filed on May 21, 2020, the entire contents of which are incorporated herein by reference.

BACKGROUND

(a) Technical Field

The present disclosure relates to a vehicle and a safe driving assistance method therefor.

(b) Description of the Related Art

An autonomous vehicle refers to a vehicle capable of driving itself by determining a risk by recognizing a driving environment and planning a driving route without a driver's operation. The level of automation of such an autonomous vehicle may be classified into six levels, from level 0 to level 5, according to criteria proposed by the Society of Automotive Engineers (SAE).

According to the SAE classification system, vehicles of level 3 and level 4 perform autonomous driving under limited conditions and transfer control of the vehicle to a driver in an emergency. A vehicle of level 5 can drive without driver intervention. When using a vehicle of level 3 to level 5, it is possible that a user (that is, a driver) will board the vehicle in a state in which it is difficult (i.e., the driver is in an "impaired state") to safely drive due to drinking or drugs. When the driver in the impaired state uses an autonomous vehicle of level 3 or level 4, it is difficult to secure safety of occupants of the vehicle because the driver cannot adequately cope in an emergency.

SUMMARY

An aspect of the present disclosure provides a vehicle that supports safe driving by determining whether a user is impaired using various devices mounted on the vehicle and a safe driving assistance method therefor.

The technical problems to be solved by the present inventive concept are not limited to the aforementioned problems, and any other technical problems not mentioned herein will be clearly understood from the following description by those skilled in the art to which the present disclosure pertains.

According to an aspect of the present disclosure, a vehicle includes a processing device that detects an authentication device approaching the vehicle, determines whether a user is impaired based on user condition information acquired using at least one device mounted on the vehicle, and performs a safe driving assistance service.

The user condition information may include at least one of walking information, speech information, driver monitoring information, or biometric information of a user.

The processing device may determine whether the user in a driving dangerous condition using at least one sensor mounted on the vehicle or a mobile terminal possessed by the user.

The processing device may calculate a guide pattern following matching degree of the user by emitting a guide pattern around the vehicle when it is determined that the user is in the driving dangerous condition, and determine whether to perform a main check for a user condition according to the guide pattern following matching degree.

The processing device may calculate a driving risk degree of the user based on weighting and scoring criteria for each information stored in a storage when the guide pattern following matching degree is less than a reference value The processing device may update vehicle history and user history information based on the calculated driving risk degree when the driving risk degree is less titan a first reference value.

The processing device may output a first-phase warning when the driving risk degree exceeds the first reference value and is less titan a second reference value.

The processing device may additionally perform a user test when the driving risk degree exceeds the second reference value.

The processing device may output a second-phase warning when the user has not passed at least one item of test items included in the user test.

The processing device may identify a user's intention to start the vehicle and take a subsequent action when the user attempts to start the vehicle after output of the second-phase warning.

According to another aspect of the present disclosure, a safe driving assistance method for a vehicle includes detecting an authentication device approaching the vehicle, determining a user's impaired state based on user condition information acquired using at least one device mounted on the vehicle, and performing a safe driving assistance service.

The user condition information may include at least one of walking information, speech information, driver monitoring information, or biometric information of the user.

The safe driving assistance method may further include determining whether the user is in the driving dangerous condition using at least one sensor mounted on the vehicle or a mobile terminal possessed by the user when the authentication device is detected.

The safe driving assistance method may further include calculating a guide pattern following matching degree of the user by emitting a guide pattern around the vehicle when it is determined that the user is in the driving dangerous condition, and determining whether to perform a main check for a user condition according to the guide pattern following matching degree.

The performing of the safe driving assistance service may include calculating a driving risk degree of the user using the user condition information based on weighting and scoring criteria for each information stored in storage when the guide pattern following matching degree is less than a reference value.

The performing of the safe driving assistance service may include determining whether the driving risk degree is less than or equal to the first reference value, and updating vehicle history and user history information based on the calculated driving risk degree when the driving risk degree is less than the first reference value.

The performing of the safe driving assistance service may include determining whether the driving risk degree exceeds the first reference value and is less than a second reference value when the driving risk degree is not less than the first reference value.

The performing of the safe driving assistance service may include further comprising: outputting a first-phase warning when the driving risk degree exceeds the first reference value and is less than the second reference value.

The performing of the safe driving assistance service may further include additionally performing a user test when the driving risk degree exceeds the second reference value, and outputting a second-phase warning when the user has not passed at least one item of test items included in the user test.

The performing of the safe driving assistance service may further comprising identifying a user's intention to start the vehicle and take a subsequent action when the user attempts to start the vehicle after output of the second-phase warning.

BRIEF DESCRIPTION OF THE DRAWINGS

The above and other objects, features and advantages of the present disclosure will be more apparent from the following detailed description taken in conjunction with the accompanying drawings:

FIG. 4 is an exemplary view showing a weighting and scoring criteria table for collected information according to an embodiment of the present disclosure;

FIG. 5 is an exemplary view for describing a method of calculating a driving risk degree according to an embodiment of the present disclosure;

DETAILED DESCRIPTION

Figure 1:
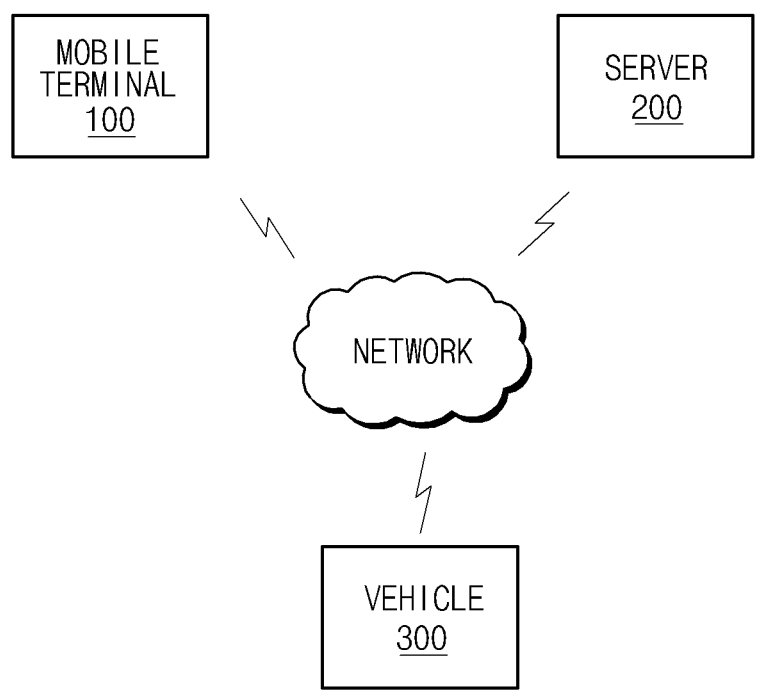
FIG. 1 is a configuration diagram of an autonomous driving assistance system according to an embodiment of the present disclosure.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, anchor components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy-disks, flash drives, smart cards and optical data storage devices. The computer readable medium can also be distributed in network coupled computer systems so that the computer readable media is stored and executed in a distributed fashion, e g, by a telematics server or a Controller Area Network (CAN).

Hereinafter, some embodiments of the present disclosure will be described in detail with reference to the exemplary drawings. In adding reference numerals to the components of each drawing, it should be noted that the same reference numerals are assigned to the same components as much as possible even though they are shown in different drawings. In addition, in describing the embodiment of the present disclosure, if it is determined that the detailed description of the related known configuration or function interferes with the understanding of the embodiment of the present disclosure, the detailed description thereof will be omitted.

In describing the components of the embodiment according to the present disclosure, terms such as first, second "A", "B", (a), (b), and the like may be used. These terms are merely intended to distinguish one component from another component, and the terms do not limit the nature, sequence or order of the constituent components. Unless otherwise defined all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless dearly defined as having such in the present application.

In the present specification, an impaired state may refer to a state in which a user (that is, a driver) cannot safely drive a vehicle, and may include a drunken state, a drugged state, anchor an overworked state. Previous user condition information may refer to information that a user is able to acquire using a portable mobile terminal, and user condition information may refer to information capable of being acquired using various devices mounted on an autonomous vehicle. Big data information may include, for example, the drinking place and drinking time of a user, the drinking place and drinking time of at least one another person, a vehicle history (e g, an existing score and the number of warnings), and/or a user history (e g, an existing score and the number of warnings), which are cumulatively collected.

Figure 2:
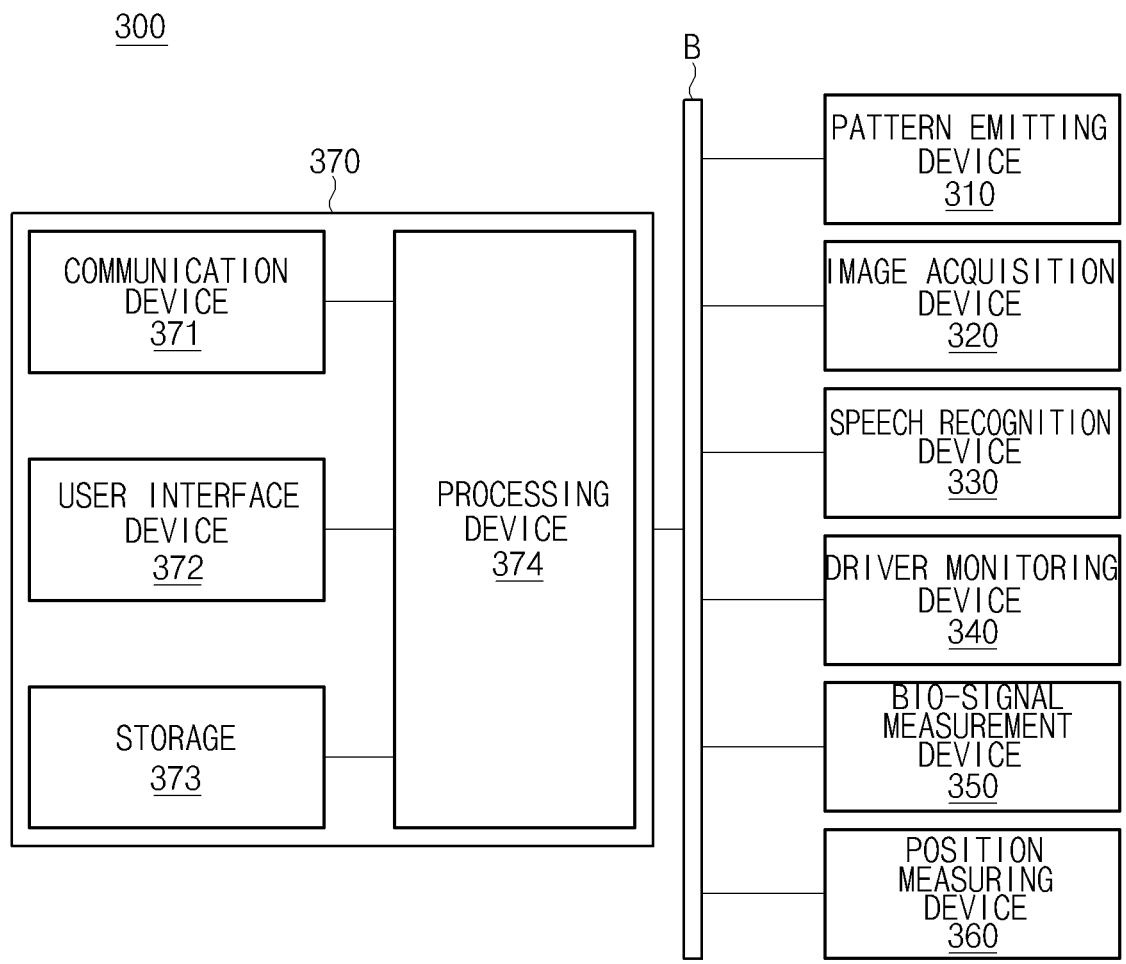
FIG. 2 is a block configuration diagram of a vehicle according to an embodiment of the present disclosure.
Figure 3:
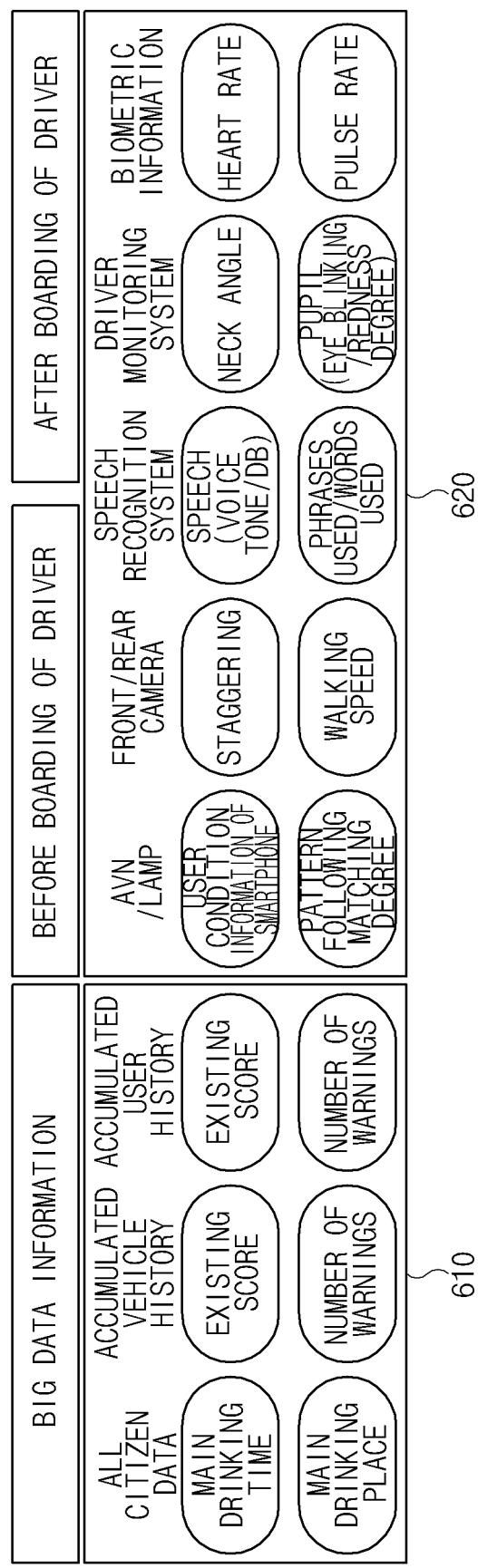
FIG. 3 is a view for describing information collection according to an embodiment of the present disclosure.

FIG. 1 is a configuration diagram of an autonomous driving assistance system according to an embodiment of the present disclosure, and FIG. 2 is a block configuration diagram of a vehicle according to an embodiment of the present disclosure. FIG. 3 is a view for describing information collection according to an embodiment of the present disclosure, FIG. 4 is an exemplary view showing a weighting and scoring criteria table for collected information according to an embodiment of the present disclosure, and FIG. 5 is an exemplary view for describing a method of calculating a driving risk degree according to an embodiment of the present disclosure.

Referring to FIG. 1, an autonomous driving support system may include a mobile terminal 100, a server 200, and a vehicle 300 which are connected through a network.

The mobile terminal 100 may be an electronic device that is portable to a user (that is, a driver), and may include a smart phone, a wearable device, a tablet, a personal digital assistant (PDA), a portable multimedia player (PMP) anchor a notebook computer. For example, the mobile terminal 100 may include a communication module, a user input module, an output module, a processor, and a memory. The communication module may enable the mobile terminal 100 to communicate with the server 200 anchor the vehicle 300, and the user input module may be for receiving data, commands or the like from a user. The processor may execute an application (hereinafter, an app) stored in a memory.

The mobile terminal 100 may identify whether or not a user is in a drunken and/or drowsy state through a sobriety detection app and/or a driver condition measurement app. The mobile terminal 100 may acquire the user's previous condition information (previous user condition information) by using sensors (e g, a camera, a gyro sensor, anchor a bio-signal measurement sensor) mounted in the terminal. For example, the sobriety detection app installed in the mobile terminal 100 in advance may measure a walking pattern (staggering) and/or a walking speed using the sensors mounted in the mobile terminal 100. The sobriety detection app may calculate the user's drunken state (i.e., impairment due to alcohol consumption, or "drunken possibility") as having e.g., a drunken possibility of 90% in consideration of the measured walking pattern and walking speed, and transmit the calculated drunken possibility to the vehicle 300.

The server 200 may create and manage a database for a visit history of the user, a visit history of at least one another person, an evaluation history indicating that safe driving of a vehicle is impaired, and/or a an evaluation history indicating that safe driving of the user is impaired. Here, the visit history may include a visit date, a visit place, a visit time, and/or a time spent. The evaluation history indicating that safe driving of a vehicle is impaired may include an evaluation date, a driving risk degree (a vulnerability score indicating impairment to safe driving), anchor whether a warning is output.

The server 200 may analyze previously collected information through big data analysis. For example, the server 200 may analyze the visit history of the user to identify the user's main drinking place and drinking time. The server 200 may analyze the evaluation history indicating that safe driving of a vehicle is vulnerable to identify the average of a driving risk degree of the vehicle and the number of warnings.

The vehicle 300 may be a vehicle capable of autonomous driving, and may include a pattern emitting device 310, an image acquisition device 320, a speech recognition device 330, a driver monitoring device 340, and a bio-signal measurement device 350, a position measuring device 360 and a vehicle terminal device 370, which are connected through a bus (B). A network connected through the bus (B) may be implemented with at least one of communication technologies such as Controller Area Network (CAN), Media Oriented Systems Transport (MOST) network, Local Interconnect Network (LIN), Ethernet, and X-by-Wire (Flexray).

The pattern emitting device 310 may emit a guide pattern to the floor around the vehicle according to an instruction from the vehicle terminal device 370. The pattern emitting device 310 may emit the guide pattern using a headlight. For example, the pattern emitting device 310 may emit the guide pattern by adjusting an emitting angle of the headlight and placing a guide pattern mask in front of the headlight. The pattern emitting device 310 may emit the guide pattern using at least one LED (Light Emitter Diode) separately provided.

The image acquisition device 320 may acquire an image for surroundings of the vehicle through at least one camera installed in the vehicle 300. The camera may be implemented with at least one image sensor among an image sensors such as charge coupled device (CCD) image sensor, a complementary metal oxide semi-conductor (CMOS) image sensor, a charge priming device (CPD) image sensor, and a charge injection device (CID) image sensor. The camera may include an image processor that performs image processing such as noise removal, color reproduction, file compression, image quality adjustment, and saturation adjustment on an image acquired through the image sensor.

The speech recognition device 330 may recognize the user's speech through a microphone installed in the vehicle 300. The speech recognition device 330 may recognize words used by the user by using speech recognition technology. Here, at least one of various known speech recognition technologies may be selectively used as the speech recognition technology, and thus a detailed description of the speech recognition process is omitted.

The speech recognition device 330 may measure a user's voice tone (pitch range) anchor a voice volume (dB). The speech recognition device 330 may recognize the voice tone and voice volume of the user through analysis of the waveform and spectrum of a voice input through the microphone.

The driver monitoring device 340 may monitor the user seated in the driver's seat using a camera mounted in front of the driver's seal. The driver monitoring device 340 may measure an eye blinking rate, an eyelid closure degree, and/or a neck angle of the user.

The bio-signal measurement device 350 may measure bio-information of the user using a bio-signal sensor mounted on the vehicle 300. Here, the bio-information may include a heart rate anchor pulse rate.

The position measuring device 360 may measure a current position (a position at the present time) of the vehicle. The position measuring device 360 may measure a position of the vehicle using at least one of positioning techniques such as Global Positioning System (GPS), Dead Reckoning (DR), Differential GPS (DGPS), and Carrier Phase Differential GPS (CDGPS).

The vehicle terminal device 370 may be implemented with an audio, video, navigation (AVN) or infotainment device mounted on the vehicle 300. The vehicle terminal device 370 may include a communication device 371, a human interface device 372, storage 373, and a processing device 374.

The communication device 371 may perform wired and/or wireless communication. As a wired communication technology, a local area network (LAN), a wide area network (WAN), an Ethernet, anchor an integrated services digital network (ISDN) may be used and as a wireless communication technology, vehicle to Everything (V2X), wireless Internet, and/or mobile communication may be used. Here, as the V2X technology, vehicle to vehicle (V2V), vehicle to infrastructure (V2I), Vehicle-to-Nomadic Devices (V2N), and/or In-vehicle communication (IVN)

may be applied. As the wireless Internet technology, at least one of communication technologies such as telematics, wireless LAN (WLAN) (WiFi), wireless broadband (Wibro), and World Interoperability for Microwave Access (Wimax) may be used. As the mobile communication technology, at least one of communication technologies such as Code Division Multiple Access (CDMA), Global System for Mobile communication (GSM), Long Term Evolution (LTE), and International Mobile Telecommunication (IMT)-2020 may be used.

The human interface device 372 may receive a user input from the input device and output a progress state and a result according to the operation of the processing device 374 to the output device. The input device may generate input data according to an operation of the user, and may be implemented with a keyboard, a keypad, a button, a switch, a touch pad, anchor a touch screen. The output device is for performing output in the form of visual information, audible information and/or tactile information, and may include a display, a sound output module, a tactile feedback output module, or the like.

The storage 373 may store software programmed to cause the processing device 374 to execute a predetermined operation, and temporarily store input data anchor output data of the processing device 374. The storage 373 may store software programmed to perform the following driving and/or autonomous driving of the vehicle. The storage 373 may store precision map information. The precision map be automatically updated at predetermined intervals or manually updated by the user.

The storage 373 may be implemented with at least one storage medium (recording medium) of storage media such as a flash memory, a hard disk, an SD card (Secure Digital Card), a random access memory (RAM), a static random access memory (SRAM), a ROM, a Programmable Read Only Memory (PROM), an Electrically Erasable and Programmable ROM (EEPROM), an Erasable and Programmable ROM (EPROM), a register, a removable disk and a web storage.

The processing device 374 may control overall operation of the vehicle and be implemented with at least one of an application specific integrated circuit (ASIC), a digital signal processor (DSP), a programmable logic device (PLD), field programmable gate array (FPGAs), a central processing unit (CPU), microcontrollers, and microprocessors.

When the user (that is, the driver) parks the vehicle 300 and gets off the vehicle after turning off the power of the vehicle, the processing device 374 may identify whether there is approach of an authentication device. When the processing device 374 receives an interrupt signal informing the approach of the authentication device from an authentication device control device (not shown), the processing device 374 may determine that there is the approach of the authentication device. Here, the authentication device may be implemented with a mechanical key, a digital key, a smart key or a smart phone key.

When the approach of the authentication device is detected, the processing device 374 may perform pre-check on the user's condition to provide a safe driving assistance service. Here, the safe driving assistance service may be a service that identifies whether a user is impaired to safe driving and provides a warning, guidance on an impaired state, anchor restrictions on vehicle driving when the user is impaired to safe driving. When there is the approach of the authentication device, the processing device 374 may identify the user's condition using the mobile terminal 100 possessed by the user. For example, the mobile terminal 100 may evaluate the user's state of impairment due to consumption of alcohol (or "drunken possibility") through the sobriety detection app installed in the terminal and transmit an evaluation result to the vehicle 300. Here, the evaluation result may be provided as a degree of the drunken possibility, a score of the drunken possibility, or whether there is impairment.

When the user condition cannot be identified using the mobile terminal 100, that is, when the mobile terminal 100 does not have a function for measuring the user condition, the processing device 374 may omit the pre-check procedure or evaluate guide pattern following of the user by emitting the guide pattern.

The processing device 374 may determine whether the user is in a driving dangerous condition (e g, whether or not there is a drunken possibility) based on previous user condition information acquired through the mobile terminal 100. The processing device 374 may control the pattern emitting device 310 and emit the guide pattern on the surrounding floor of the vehicle 300 to induce the user's following when it is determined that the user is in a driving dangerous condition. The processing device 374 may operate the image acquisition device 320 to capture and store an image representing that the user follows the guide pattern. The processing device 374 may analyze the image acquired through the image acquisition device 320 to evaluate the user's following for the guide pattern. In other words, the processing device 374 may calculate the user's guide pattern following accuracy (pattern following matching degree).

The processing device 374 may determine whether the user is impaired to safe driving based on the user's guide pattern following accuracy. The processing device 374 may determine that the user is not impaired to safe driving (an in-impaired state) when the user's guide pattern following accuracy is greater than or equal to a reference accuracy. The processing device 374 may determine that the user is impaired to safe driving when the user's guide pattern following accuracy is less than the reference accuracy. The processing device 374 may terminate the safe driving assistance service when it is determined that the user is not impaired to safe driving. For example, the processing device 374 may determine that the user is not impaired to safe driving when the user's guide pattern following accuracy is 90% or more, and terminate the safe driving assistance service.

When it is determined that the user is impaired to safe driving, the processing device 374 may perform a main check on the user's condition. The processing device 374 may collect big data information and user condition information at the start of the main check. Referring to FIG. 3, big data information 610 may include a main drinking time and a main drinking place of at least one another user (another person), a vehicle history and/or a user history. Also, the big data information 610 may further include a main drinking place and a main drinking time of the user. The main drinking place may be determined based on the number of visits to the drinking place, and the main drinking time may be determined based on the number of times of drinking by hour. The vehicle history may include an average of the driving risk degree calculated by the vehicle anchor the number of outputs of warning indicating that the user is impaired to safe driving. The user history may include an average of the driving risk degree evaluated for the user anchor the number of warnings of an impaired state of the user. User condition information 620 may include walking information (e g, staggering and walking speed) obtained before and after boarding of a driver (user), speech information (e g voice tone, voice volume, phrases used, and/or words used), driver monitoring information (e.g., an neck angle anchor pupil information), and/or bio-information. The user condition information 620 may further include the previous user condition information received from the mobile terminal 100 and a guide pattern following accuracy-evaluated during the pre-check.

The processing device 374 may receive the big data information 610 provided from the server 200 through the communication device 371. The processing device 374 may collect user condition information 620 using at least one of the image acquisition device 320, the speech recognition device 330, the driver monitoring device 340, or the bio-signal measurement device 350. The processing device 374 may detect walking information such as a user's walking pattern (whether the user staggered) anchor walking speed by analyzing an image acquired through the image acquisition device 320. The processing device 374 may detect speech information such as the user's voice tone, voice volume, anchor words used (and/or phrases) through the speech recognition device 330. The processing device 374 may detect driver monitoring information, such as the user's neck angle, an eye blinking rate, an eyelid closure degree, and/or a degree of eye redness using the driver monitoring device 340. The processing device 374 may detect biometric information, such as the user's heart rate anchor pulse rate using the bio-signal measurement device 350.

The processing device 374 may calculate a driving risk degree of the user based on user condition information and the big data information. The processing device 374 may calculate the driving risk degree by referring to a weighting and scoring criteria table for each information pre-stored in the storage 373. For example, the processing device 374 may calculate the driving risk degree based on the weighting and scoring criteria defined in the weighting and scoring criteria table for each information shown in FIG. 4.

Next, a method for calculating a driving risk degree will be described with reference to FIGS. 4 and 5. The processing device 374 may perform the main check when there is a drunken possibility, the drunken possibility score is 8 points, and the guide pattern following score is 40% as a result of determination by a smartphone, received from the mobile terminal 100 in tire pre-check. The processing device 374 may calculate a score for each information based on the weighting and scoring criteria defined in the weighting and scoring criteria table for each information shown in FIG. 4. For example, as shown in FIG. 5, in a case where 10 points when the walking speed is lowered by 2 kph than the reference speed of 4 kph, 3 points when a predetermined specific word is used 3 times, 10 points when the voice volume is 70 dB greater than the reference volume 40 dB by 30 dB, 10 points when the neck angle indicates that drowsiness occurs, 10 points when there is no blinking and occurrence of drowsiness is determined, 9 points by comparing a stop location "Gangnam" and a spent time "Friday 19:00 to 22:00" with big data information, 4 points that is a score according to the vehicle history, and 8 points that is a score according to the user history, it is possible to calculate 5.85 points as the driving risk degree (driving risk score) by applying weights to the scores.

The processing device 374 may perform output of a warning, guidance on an impaired state of the user, and/or driving restrictions on a vehicle according to the driving risk degree of the user. When the driving risk degree is less than or equal to a first reference value (e.g., 3 points), the processing device 374 may update the driving risk degree by reflecting the driving risk degree calculated previously in the vehicle history and user history information. Thereafter, when the user starts the vehicle, the processing device 374 may terminate the safe driving assistance service. On the other hand, when the user does not start the vehicle for a certain period of time, the processing device 374 may turn off the power of the vehicle or terminate the safe driving assistance service.

The processing device 374 may output a first phase warning when the driving risk degree exceeds a first reference value and is equal to or less than a second reference value (e.g., 5 points). The processing device 374 may output a warning indicating that the user is in an impaired state. For example, the processing device 374 may output a warning message such as "You may have a drunken possibility. Would you like to call a designated driver?" and provide a list of designated driver companies.

When the driving risk degree of the user exceeds the second reference value, the processing device 374 may further perform a test for the user. In this case, the processing device 374 may perform at least one user test. For example, the processing device 374 may provide at least one puzzle game and determine whether the user completes all puzzles within a predetermined period of time.

The processing device 374 may output a first-phase warning when the user passes all user tests which are additionally provided. Meanwhile, the processing device 374 may output a second-phase warning when the user has not passed all user tests which are additionally provided. For example, the processing device 374 may output a warning message such as "There is a high drunken possibility. Please call a designated driver" on the display and output a speech guidance at the same time. In addition, the processing device 374 may additionally provide a button for automatically connecting to a designated driver.

When the user attempts to start the vehicle after outputting the second-phase warning, the processing device 374 may again identify the user's intention to start the vehicle. The processing device 374 may output a message such as "If you still want to start vehicle, try restarting vehicle again." The processing device 374 may terminate the safe driving assistance service and start the vehicle when the user intends to start the vehicle. The processing device 374 may continuously monitor the user in a state in which the vehicle is started. When the user does not intend to start the vehicle, the processing device 374 may wait for a predetermined time, terminate the safe driving assistance service, and turn off a power supply of the vehicle.

Figure 6:
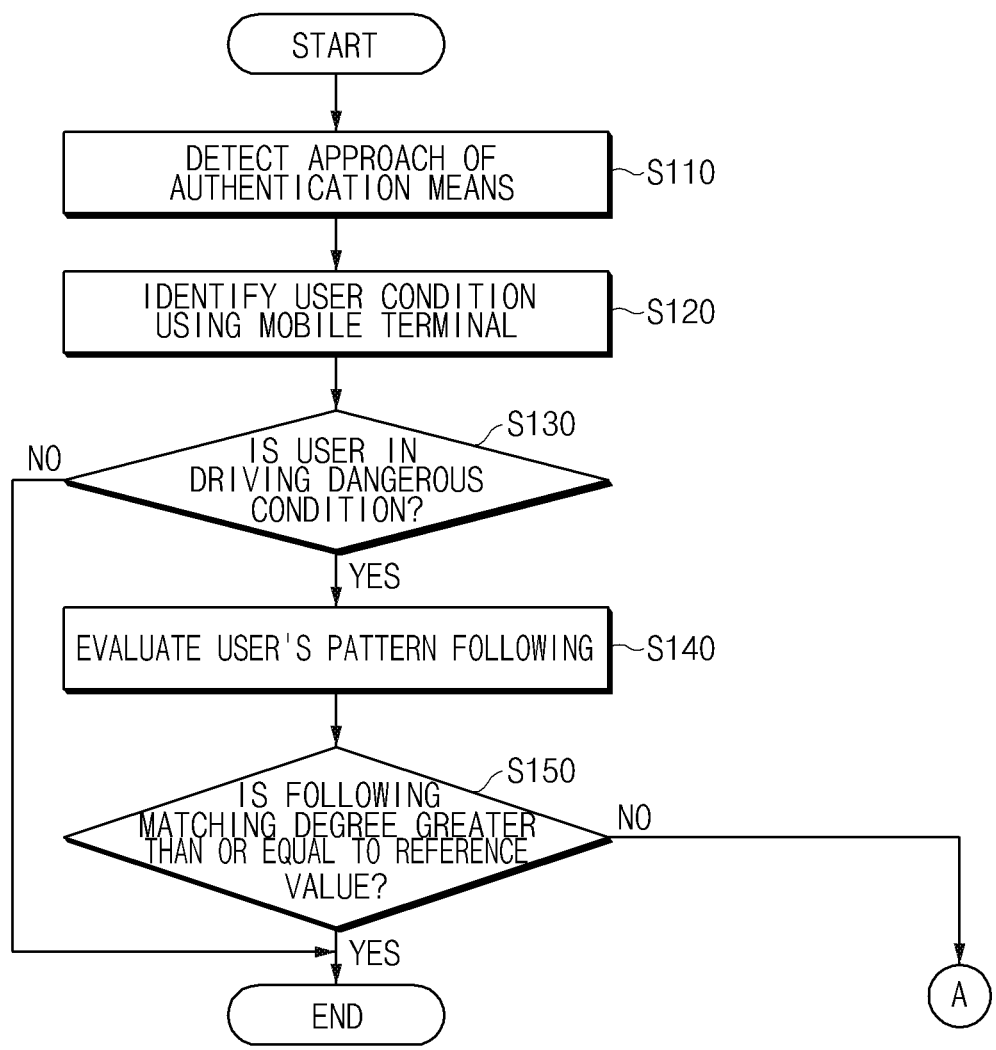
FIGS. 6 and 7 are flowcharts of a method for supporting safe driving of a vehicle according to an embodiment of the present disclosure.
Figure 7:
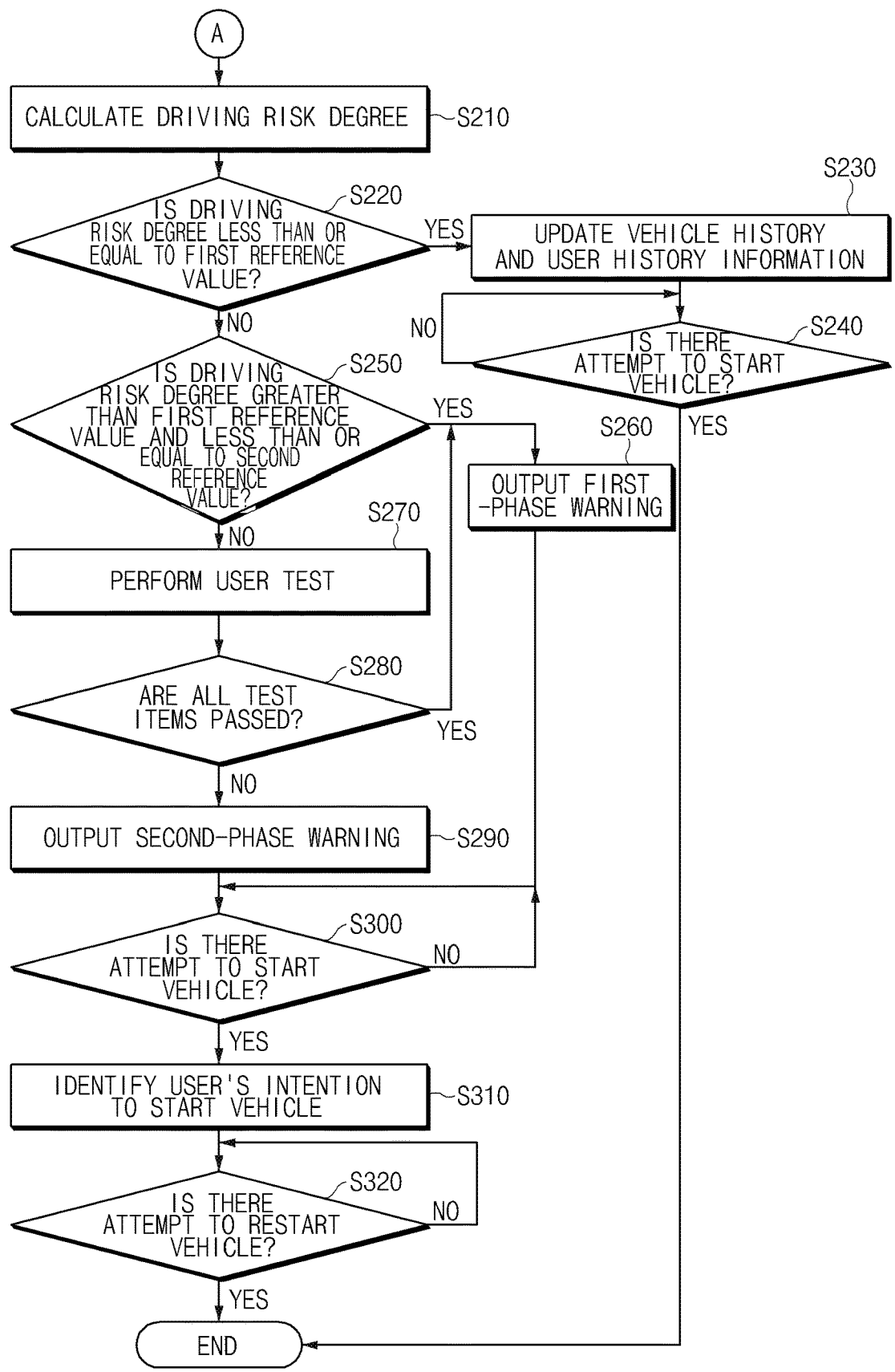

FIGS. 6 and 7 are flowcharts of a method for supporting safe driving of a vehicle according to an embodiment of the present disclosure.

The processing device 374 of the vehicle 300 may detect the approach of the authentication device (SI 10). The processing device 374 may recognize that the authentication device is approaching the vehicle when receiving an interrupt signal transmitted from a control device of the authentication device. The processing device 374 may execute the safe driving assistance service when the approach of the authentication device is detected.

The processing device 374 may identify a user condition using the mobile terminal 100 (S120). The mobile terminal 100 may determine the user condition using the user condition measurement app installed in the terminal and transmit a result of the determination to the processing device 374 as previous user condition information. For example, the mobile terminal 100 may evaluate a drunken possibility of the user through the sobriety detection app installed in the terminal and transmit a result of the evaluation to the vehicle 300. Here, the result of the evaluation may be provided as a degree of drunken possibility, a drunken possibility score, or whether there is a drunken possibility.

The processing device 374 may determine whether the user is in a driving dangerous condition based on the user condition identified through the mobile terminal 100 (S130). The processing device 374 may determine whether the user is in the driving dangerous condition based on the previous user condition information provided from the mobile terminal 100.

When it is determined that the user is in the driving dangerous condition, the processing device 374 may perform evaluation of the user's guide pattern following (S140). The processing device 374 may control the pattern emitting device 310 and emit the guide pattern on the surrounding floor of the vehicle 300 to induce the user's following when it is determined that the user is in a driving dangerous condition. The processing device 374 may operate the image acquisition device 320 to capture and store an image representing that the user follows the guide pattern. The processing device 374 may analyze the image acquired through the image acquisition device 320 to evaluate the user's guide pattern following. The processing device 374 may calculate an accuracy with which the user follows the guide pattern, that is, the pattern following matching degree.

The processing device 374 may determine whether the guide pattern following matching degree of the user is greater than or equal to a reference value (S150). In other words, it may be determined that the user is not impaired to safe driving (an un-impaired state) when the user's guide pattern following accuracy is greater than or equal to a reference accuracy. The processing device 374 may determine that the user is impaired to safe driving when the user's guide pattern following accuracy is less than the reference accuracy. The processing device 374 may finish the safe driving assistance service when it is determined that the user is not impaired to safe driving. For example, the processing device 374 may determine that the user is not impaired to safe driving when the user's guide pattern following accuracy is 90% or more, and terminate the safe driving assistance service.

When it is determined that the user is in a impaired state, the processing device 374 may calculate the driving risk degree of the user based on the user condition information and the big data information (S210). The processing device 374 may acquire big data information by communicating with the server 200. The big data information may include a main drinking place and a main drinking time of the user, a main drinking time and a main drinking place of at least one another user (another person), a vehicle history and/or a user history. The processing device 374 may acquire user condition information using at least one of the image acquisition device 320, the speech recognition device 330, the driver monitoring device 340, or the bio-signal measurement device 350. The user condition information may include walking information (e g, staggering and walking speed) obtained before and after boarding of a driver (user), speech information (e g voice tone, voice volume, phrases used, anchor words used), driver monitoring information (e g, an neck angle and/or pupil information and/or bio-information. The user condition information may further include the previous user condition information received from the mobile terminal 100 and a guide pattern following accuracy evaluated during the pre-check. The processing device 374 may calculate the driving risk degree based on a weight and a scoring reference for each information, which are pre-stored in the storage 373.

The processing device 374 may determine whether the driving risk degree is equal to or less than a first reference value (e g, 3 points) (S220). When the driving risk degree is less than or equal to the first reference value (e g, 3 points), the processing device 374 may update the driving risk degree by reflecting the driving risk degree calculated previously in the vehicle history and user history information.

The processing device 374 may determine whether there is an attempt to start the vehicle by the user (S240). When the user starts the vehicle, the processing device 374 may terminate the safe driving support service. In addition, when the user does not start the vehicle for a certain period of time, the processing device 374 may turn off a power supply of the vehicle or terminate the safe driving assistance service.

The processing device 374 may determine whether a driving risk degree is less than or equal to a second reference value (e g, 5 points) when the driving risk degree exceeds the first reference value (S250). The processing device 374 may output a first-phase warning when the driving risk degree is equal to or less than the second reference value (S260). The processing device 374 may output a warning indicating that the user is in an impaired state. For example, the processing device 374 may output a warning message such as "You may have a drunken possibility. Would you like to call a designated driver?" and provide a list of designated driver companies.

When a driving risk degree of the user exceeds the second reference value, the processing device 374 further tests the user (S270). In this case, the processing device 374 may perform at least one user test. For example, the processing device 374 may provide at least one puzzle game and determine whether the user completes all puzzles within a predetermined period of time.

The processing device 374 may determine whether the user passes all test items (S280). The processing device 374 may determine whether the user passes all user tests which are additionally provided. When the user has passed all test items, the processing device 374 may output a first-phase warning (S260).

Meanwhile, when the user does not pass all test items, the processing device 374 may output a second-phase warning (S290). For example, the processing device 374 may output a warning message such as "There is a high drunken possibility. Please call a designated driver" on the display and output a speech guidance at the same time. In addition, the processing device 374 may additionally provide a button for automatically connecting to a designated driver.

The processing device 374 may output the second-phase warning and then determine whether the user attempts to start the vehicle (S300). When the user attempts to start the vehicle, the processing device 374 may identify the user's intention to start the vehicle (S310). The processing device 374 may output a message such as "If you still want to start vehicle, try restarting vehicle again."

In S320, the processing device 374 may terminate the safe driving assistance service and start the vehicle when the user intends to start the vehicle as a result of the identification. The processing device 374 may continuously monitor the user in a state in which the vehicle is started. When the user does not intend to start the vehicle, the processing device 374 may wait for a predetermined period of time, terminate the safe driving assistance service, and turn off the power supply of the vehicle.

Figure 8:
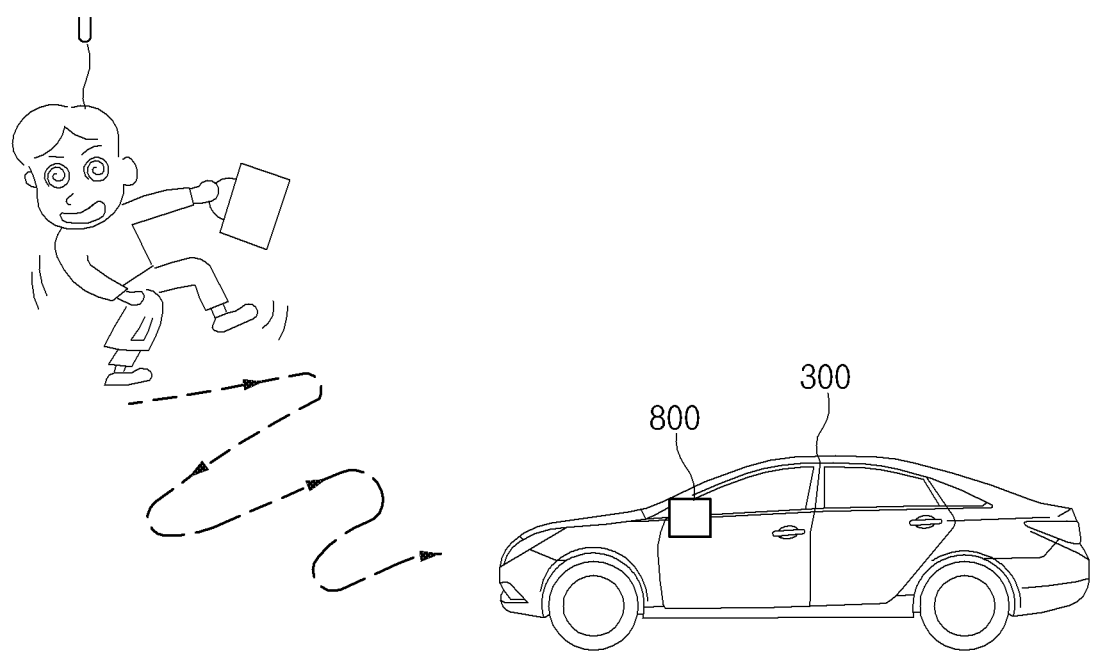
FIG. 8 is a view for explaining a method of identifying a driving dangerous condition of a user according to another embodiment of the present disclosure.

Although it is described that whether the user is in a driving dangerous condition is determined using the mobile terminal 100 carried by the user when an authentication device (e.g., a smart key) approaching the vehicle 300 is detected in the above-described embodiment, the present disclosure is not limited thereto, and may be implemented to determine whether a user is in a driving dangerous condition by using at least one sensor mounted on the vehicle 300. Referring to FIG. 8, when the user (U) approaches the vehicle 300, the vehicle 300 may detect the authentication device possessed by the user (U), and thus recognize the approach of the user (U). When the approach of the authentication device is detected, the vehicle 300 may detect walking information of the user (U), that is, a walking pattern anchor a walking speed using a sensor 800 mounted on the vehicle 300, for example, a camera anchor a radar. The vehicle 300 may determine whether the user (U) is in a driving dangerous condition based on the detected walking information. For example, the vehicle 300 may determine that the user is in a driving dangerous condition when the walking pattern of the user (U) is a zigzag pattern and the walking speed is less than a preset reference speed.

According to the above-described embodiments, the vehicle 300 may analyze the behavior and condition of the user before and after boarding using devices necessary for autonomous driving to provide a service suitable for the user's impaired state, thus inducing safe driving of the user.

The above description is merely illustrative of the technical idea of the present disclosure, and various modifications and variations may be made without departing from the essential characteristics of the present disclosure by those skilled in the art to which the present disclosure pertains. Accordingly, the embodiment disclosed in the present disclosure is not intended to limit the technical idea of the present disclosure but to describe the present disclosure, and the scope of the technical idea of the present disclosure is not limited by the embodiment. The scope of protection of the present disclosure should be interpreted by the following claims, and all technical ideas within the scope equivalent thereto should be construed as being included in the scope of the present disclosure.

According to the present disclosure, it is possible to induce safe driving by providing a service suitable for a user's impaired state by analyzing a user's behavior before and after boarding using various devices mounted on a vehicle.

Further, according to the present disclosure, it is possible to strengthen vehicle safety-management of the vehicle owner when an autonomous vehicle is used as a shared vehicle.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. A vehicle, comprising:
a processing device configured to:
detect an authentication device approaching the vehicle,
determine whether a user is in a driving dangerous condition based on user condition information acquired using at least one device mounted on the vehicle,
calculate a guide pattern following matching degree of the user by emitting a guide pattern around the vehicle when it is determined that the user is in the driving dangerous condition,
determine a user's impaired state based on the guide pattern following matching degree, and
perform a safe driving assistance service.

2. The vehicle of claim 1, wherein the user condition information includes at least one of walking information, speech information, driver monitoring information, or biometric information of a user.

3. The vehicle of claim 1, wherein the processing device is configured to perform a main check for a user condition when it is determined that the user is impaired to safe driving.

4. The vehicle of claim 1, wherein the processing device is configured to calculate a driving risk degree of the user based on weighting and scoring criteria for each information stored in storage when the guide pattern following matching degree is less than a reference value.

5. The vehicle of claim 4, wherein the processing device is configured to update vehicle history and user history information based on the calculated driving risk degree when the driving risk degree is less than a first reference value.

6. The vehicle of claim 5, wherein the processing device is configured to output a first-phase warning when the driving risk degree exceeds the first reference value and is less than a second reference value.

7. The vehicle of claim 6, wherein the processing device is configured to additionally perform a user test when the driving risk degree exceeds the second reference value.

8. The vehicle of claim 7, wherein the processing device is configured to output a second-phase warning when the user has not passed at least one item of test items included in the user test.

9. The vehicle of claim 8, wherein the processing device is configured to identify a user's intention to start the vehicle and take a subsequent action when the user attempts to start the vehicle after output of the second-phase warning.

10. A safe driving assistance method for a vehicle, comprising:
detecting, by a processing device in the vehicle, an authentication device approaching the vehicle;
determining, by the processing device whether the user is in a driving dangerous condition base on user condition information acquired using at least one device mounted on the vehicle when the authentication device is detected;
calculating a guide pattern following matching degree of the user by emitting a guide pattern around the vehicle when it is determined that the user is in the driving dangerous condition;
determining, by the processing device, a user's impaired state based on the guide pattern following matching degree; and
performing, by the processing device, a safe driving assistance service.

11. The safe driving assistance method of claim 10, wherein the user condition information includes at least one of walking information, speech information, driver monitoring information, or biometric information of the user.

12. The safe driving assistance method of claim 10, further comprising: performing a main check for a user condition when it is determined that the user is impaired to safe driving.

13. The safe driving assistance method of claim 10, wherein performing the safe driving assistance service includes calculating a driving risk degree of the user using the user condition information based on weighting and scoring criteria for each information stored in storage when the guide pattern following matching degree is less than a reference value.

14. The safe driving assistance method of claim 13, wherein performing the safe driving assistance service includes:
- determining whether the driving risk degree is less than or equal to the first reference value, and
- updating vehicle history and user history information based on the calculated driving risk degree when the driving risk degree is less than the first reference value.

15. The safe driving assistance method of claim 14, wherein performing the safe driving assistance service includes determining whether the driving risk degree exceeds the first reference value and is less than a second reference value when the driving risk degree is not less than the first reference value.

16. The safe driving assistance method of claim 15, wherein performing the safe driving assistance service further includes outputting a first-phase warning when the driving risk degree exceeds the first reference value and is less than the second reference value.

17. The safe driving assistance method of claim 16, wherein performing the safe driving assistance service further includes:
- additionally performing a user test when the driving risk degree exceeds the second reference value, and
- outputting a second-phase warning when the user has not passed at least one item of test items included in the user test.

18. The safe driving assistance method of claim 17, further comprising:
- identifying a user's intention to start the vehicle and take a subsequent action when the user attempts to start the vehicle after output of the second-phase warning.

* * * * *